US005726040A

United States Patent [19]
Ensley et al.

[11] Patent Number: 5,726,040
[45] Date of Patent: Mar. 10, 1998

[54] COSMETIC COMPOSITIONS INCLUDING TROPOELASTIN ISOMORPHS

[76] Inventors: Burt D. Ensley, 7 Colts Neck Dr., Newtown, Pa. 18940; Matthew Ludmer, 41 Indian Hill Rd., R.D. 3, Katonak, N.Y. 10536

[21] Appl. No.: 641,627

[22] Filed: May 2, 1996

Related U.S. Application Data

[63] Continuation of Ser. No. 455,647, May 31, 1995, abandoned, which is a continuation of Ser. No. 150,712, Nov. 10, 1993, abandoned.

[51] Int. Cl.$^6$ .................. C12P 21/06; A61K 7/035; A61K 7/42; A61K 38/16
[52] U.S. Cl. .................. 435/69.1; 435/252.3; 435/252.33; 435/172.3; 435/320.1; 435/325; 435/366; 435/69.7; 435/69.8; 424/401; 424/59; 424/69; 424/78.03; 514/2; 514/12; 530/350; 530/353; 935/10; 935/60; 935/66
[58] Field of Search ...................... 435/69.1, 69.7, 435/69.8, 252.33, 172.3, 320.1, 325, 366; 514/2, 12; 424/401, 59, 69, 63, 78.03; 935/10, 18, 70, 72, 73

[56] References Cited

U.S. PATENT DOCUMENTS

| | | | |
|---|---|---|---|
| 3,991,184 | 11/1976 | Kludas et al. | 514/21 |
| 4,007,266 | 2/1977 | Choay | 424/582 |
| 4,327,078 | 4/1982 | Charlet et al. | 424/45 |
| 4,474,763 | 10/1984 | Lubowe | 514/21 |
| 4,659,740 | 4/1987 | Usher | 514/773 |
| 4,783,523 | 11/1988 | Urry et al. | 530/323 |
| 4,898,926 | 2/1990 | Urry | 528/328 |
| 5,055,298 | 10/1991 | Kludas | 424/401 |
| 5,064,430 | 11/1991 | Urry | 623/1 |
| 5,089,406 | 2/1992 | Williams et al. | 435/172.3 |

FOREIGN PATENT DOCUMENTS

| | | |
|---|---|---|
| 63-14707 | 1/1988 | Japan. |
| WO 89/05137 | 6/1989 | WIPO. |

OTHER PUBLICATIONS

Mecham, "Elastin Synthesis and Fiber Assembly", Annal. Ny Acad. Sci, pp. 137–146.
Rosenbloom et al., "Extracellular matrix 4: The Elastic Fiber", FASEB J., 7:1208, 1993.
Stedman's Medical Dictionary, pp. 1329–1330, 25th edition. Williams & Wilkins Baltimore, MD.
Barrineau et al., "Differential expression of aortic and lung elastin genes during chick embryogenesis", Dev. Biology, 87:46–51, 1981.
Rosenbloom, "Elastin: an overview", in Biochemistry of the Major Components of the Extracellular Matrix, Academic Press, Inc., Orlando, FL, p. 172, 1987.
Rosenbloom et al., "Biology of disease", Lab. Invest., 51:605, 1984.
Wrenn et al., "Identification of multiple tropoelastins secreted by bovine cells", J. Biol. Chem., 262:2244, 1987.
The Merck Index, 1983. (Windholz et al., eds.), Merck & Co., Rahway, NY p. 2060.
Watson et al. (1987) in: Molecular Biology Of The Gene, fourth edition. Benjamn/Cummings Publishing Comparny, Baltimore, MD, p. 313.
Patent Abstracts of Japan, vol. 12 (213) 17 Jun. 1988, 163C505 Abstract #54.
Fazio et al. 1988 J. Invest. Dermatol. 91, 458–464.
Fazio et al. 1988. Lab. Invest. 58, 270–277.
Indik et al. 1990. Arch. Biochem. Biophys. 280. 80–86.
Indik et al. 1987 Proc. Natl. Acad. Sci. USA. 84, 5680–5684.

*Primary Examiner*—Christopher S. F. Low

[57] ABSTRACT

A cosmetic composition including a non naturally-occurring extracellular matrix protein in combination with a cosmetic carrier is described. The protein is preferably of human origin and has not been previously cross-linked. The protein is most preferably selected from the group consisting of soluble human procollagen and soluble human tropoelastin. The protein may include at least one additional non-naturally occurring amino acid sequence moiety, the amino acid sequence moiety selected from the group consisting of a hydrophobic sequence, a hydrophilic sequence, and a lysine-rich sequence.

A cosmetic composition in which the non naturally-occurring extracellular matrix protein is an isomorphic form of the protein is also described. The isomorph of the protein is preferably selected from the group consisting of elastin isomorphs, collagen isomorphs and fibronectin isomorphs. Most preferably, the isomorphs are of human origin and have not been previously cross-linked.

Methods of making and using a cosmetic composition of the invention are also described.

6 Claims, No Drawings

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

TTTCTCCCCG AGATGGCGGG TCTGA 25

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

ATTTCTCCCC GAGATGGCGG GTCTG 25

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CATTTCTCCC CGAGATGGCG GGTCT 25

( 2 ) INFORMATION FOR SEQ ID NO:4:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:4:

GCATTTCTCC CCGAGATGGC GGGTC       25

(2) INFORMATION FOR SEQ ID NO:5:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:5:

GGCATTTCTC CCCGAGATGG CGGGT       25

(2) INFORMATION FOR SEQ ID NO:6:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:6:

GGGCATTTCT CCCCGAGATG GCGGG       25

(2) INFORMATION FOR SEQ ID NO:7:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:7:

GGGGCATTTC TCCCCGAGAT GGCGG       25

(2) INFORMATION FOR SEQ ID NO:8:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:8:

TGGGGCATTT CTCCCCGAGA TGGCG       25

(2) INFORMATION FOR SEQ ID NO:9:

(i) SEQUENCE CHARACTERISTICS:
    (A) LENGTH: 25 base pairs
    (B) TYPE: nucleic acid
    (C) STRANDEDNESS: single (D) TOPOLOGY: linear (i i) MOLECULE TYPE: cDNA (x i) SEQUENCE DESCRIPTION: SEQ ID NO:9:

CTGGGGCATT TCTCCCCGAG ATGGC                                               25

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:10:

GCTGGGGCAT TTCTCCCCGA GATGG                                               25

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:11:

GGCTGGGGCA TTTCTCCCCG AGATG                                               25

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:12:

GGGCTGGGGC ATTTCTCCCC GAGAT                                               25

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:13:

CGGGCTGGGG CATTTCTCCC CGAGA                                               25

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:14:

AGCGGGCTGG GGCATTTCTC CCCGA                                                           25

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

AGAGCGGGCT GGGGCATTTC TCCCC                                                           25

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GAGAGCGGGC TGGGGCATTT CTCCC                                                           25

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GGAGAGCGGG CTGGGCATT TCTCC                                                            25

( 2 ) INFORMATION FOR SEQ ID NO:18:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CGGAGAGCGG GCTGGGGCAT TTCTC                                                           25

( 2 ) INFORMATION FOR SEQ ID NO:19:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

GCGGAGAGCG GGCTGGGGCA TTTCT                                                           25

( 2 ) INFORMATION FOR SEQ ID NO:20:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:20:

ACAAGCTTTC CCCAGGCAGG CCCCA        25

(2) INFORMATION FOR SEQ ID NO:21:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:21:

CCACAAGCTT TCCCCAGGCA GGCCC        25

(2) INFORMATION FOR SEQ ID NO:22:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:22:

GCCACAAGCT TCCCCAGGC AGGCC         25

(2) INFORMATION FOR SEQ ID NO:23:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:23:

GGCCACAAGC TTTCCCCAGG CAGGC        25

(2) INFORMATION FOR SEQ ID NO:24:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:24:

CGGCCACAAG CTTTCCCCAG GCAGG        25

(2) INFORMATION FOR SEQ ID NO:25:

(i) SEQUENCE CHARACTERISTICS:
    (A) LENGTH: 25 base pairs
    (B) TYPE: nucleic acid
    (C) STRANDEDNESS: single (D) TOPOLOGY: linear (i i) MOLECULE TYPE: cDNA (x i) SEQUENCE DESCRIPTION: SEQ ID NO:25:

CGGCCACAAG CTTTCCCCAG GCAGG 25

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:26:

CCGGCCACAA GCTTTCCCCA GGCAG 25

(2) INFORMATION FOR SEQ ID NO:27:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:27:

TCCGGCCACA AGCTTTCCCC AGGCA 25

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:28:

TTCCGGCCAC AAGCTTTCCC CAGGC 25

(2) INFORMATION FOR SEQ ID NO:29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:29:

TTCCGGCCAC AAGCTTTCCC CAGGC 25

(2) INFORMATION FOR SEQ ID NO:30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:30:

CTTCCGGCCA CAAGCTTTCC CCAGG                    25

( 2 ) INFORMATION FOR SEQ ID NO:31:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

TCTTCCGGCC ACAAGCTTTC CCCAG                    25

( 2 ) INFORMATION FOR SEQ ID NO:32:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

CTCTTCCGGC CACAAGCTTT CCCCA                    25

( 2 ) INFORMATION FOR SEQ ID NO:33:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

TCTCTTCCGG CCACAAGCTT TCCCC                    25

( 2 ) INFORMATION FOR SEQ ID NO:34:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

TCTCTTCCGG CCACAAGCTT TCCCC                    25

( 2 ) INFORMATION FOR SEQ ID NO:35:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

TTCTCTTCCG GCCACAAGCT TTCCC                    25

( 2 ) INFORMATION FOR SEQ ID NO:36:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:36:

| TTTCTCTTCC GGCCACAAGC TTTCC | 25 |

( 2 ) INFORMATION FOR SEQ ID NO:37:

( i ) SEQUENCE CHARACTERISTICS:
  ( A ) LENGTH: 2242 base pairs
  ( B ) TYPE: nucleic acid
  ( C ) STRANDEDNESS: both
  ( D ) TOPOLOGY: both ( i i ) MOLECULE TYPE: cDNA ( v i ) ORIGINAL SOURCE:
  ( B ) STRAIN: tropoelastin cDNA (cHE- 3)

( x i ) SEQUENCE DESCRIPTION: SEQ ID NO:37:

| CCGGGATAAA | ACGAGGTGCG | GAGAGCGGGC | TGGGGCATTT | CTCCCCGAGA | TGGCGGGTCT | 60 |
| GACGGCGGCG | GCCCCGCGGC | CCGGAGTCCT | CCTGCTCCTG | CTGTCCATCC | TCCACCCCTC | 120 |
| TCGGCCTGGA | GGGGTCCCTG | GGCCATTCC  | TGGTGGAGTT | CCTGGAGGAG | TCTTTTATCC | 180 |
| AGGGGCTGGT | CTCGGAGCCC | TTGGAGGAGG | AGCGCTGGGG | CCTGGAGGCA | AACCTCTTAA | 240 |
| GCCAGTTCCC | GGAGGGCTTG | CGGGTGCTGG | CCTTGGGGCA | GGGCTCGGCG | CCTTCCCCGC | 300 |
| AGTTACCTTT | CCGGGGCTC  | TGGTGCCTGG | TGGAGTGGCT | GACGCTGCTG | CAGCCTATAA | 360 |
| AGCTGCTAAG | GCTGGCGCTG | GGCTTGGTGG | TGTCCCAGGA | GTTGGTGGCT | TAGGAGTGTC | 420 |
| TGCAGGTGCG | GTGGTTCCTC | AGCCTGGAGC | CGGAGTGAAG | CCTGGGAAAG | TGCCGGGTGT | 480 |
| GGGGCTGCCA | GGTGTATACC | CAGGTGGCGT | GCTCCCAGGA | GCTCGGTTCC | CCGGTGTGGG | 540 |
| GGTGCTCCCT | GGAGTTCCCA | CTGGAGCAGG | AGTTAAGCCC | AAGGCTCCAG | GTGTAGGTGG | 600 |
| AGCTTTTGCT | GGAATCCCAG | GAGTTGGACC | CTTTGGGGGA | CCGCAACCTG | GAGTCCCACT | 660 |
| GGGGTATCCC | ATCAAGGCCC | CCAAGCTGCC | TGGTGGCTAT | GGACTGCCCT | ACACCACAGG | 720 |
| GAAACTGCCC | TATGGCTATG | GGCCCGGAGG | AGTGGCTGGT | GCAGCGGGCA | AGGCTGGTTA | 780 |
| CCCAACAGGG | ACAGGGGTTG | GCCCCAGGC  | AGCAGCAGCA | GCAGCAGCTA | AAGCAGCAGC | 840 |
| AAAGTTCGGT | GCTGGAGCAG | CCGGAGTCCT | CCCTGGTGTT | GGAGGGGCTG | GTGTTCCTGG | 900 |
| CGTGCCTGGG | GCAATTCCTG | GAATTGGAGG | CATCGCAGGC | GTTGGGACTC | CAGCTGCAGC | 960 |
| TGCAGCTGCA | GCAGCAGCCG | CTAAGGCAGC | CAAGTATGGA | GCTGCTGCAG | GCTTAGTGCC | 1020 |
| TGGTGGGCCA | GGCTTTGGCC | CGGGAGTAGT | TGGTGTCCCA | GGAGCTGGCG | TTCCAGGTGT | 1080 |
| TGGTGTCCCA | GGAGCTGGGA | TTCCAGTTGT | CCCAGGTGCT | GGGATCCCAG | GTGCTGCGGT | 1140 |
| TCCAGGGGTT | GTGTCACCAG | AAGCAGCTGC | TAAGGCAGCT | GCAAAGGCAG | CCAAATACGG | 1200 |
| GGCCAGGCCC | GGAGTCGGAG | TTGGAGGCAT | TCCTACTTAC | GGGGTTGGAG | CTGGGGGCTT | 1260 |
| TCCCGGCTTT | GGTGTCGGAG | TCGGAGGTAT | CCCTGGAGTC | GCAGGTGTCC | CTAGTGTCGG | 1320 |
| AGGTGTTCCC | GGAGTCGGAG | GTGTCCCGGG | AGTTGGCATT | TCCCCGAAG  | CTCAGGCAGC | 1380 |
| AGCTGCCGCC | AAGGCTGCCA | AGTACGGAGT | GGGGACCCCA | GCAGCTGCAG | CTGCTAAAGC | 1440 |
| AGCCGCCAAA | GCCGCCCAGT | TTGCTCTTCT | CAATCTTGCA | GGGTTAGTTC | CTGGTGTCGG | 1500 |
| CGTGGCTCCT | GGAGTTGGCG | TGGCTCCTGG | TGTCGGTGTG | GCTCCTGGAG | TTGGCTTGGC | 1560 |

| | | | | | |
|---|---|---|---|---|---|
| TCCTGGAGTT | GGCGTGGCTC | CTGGAGTTGG | TGTGGCTCCT | GGCGTTGGCG | TGGCTCCCGG | 1620
| CATTGGCCCT | GGTGGAGTTG | CAGCTGCAGC | AAAATAAGCT | GCCAAGGTGG | CTGCCAAAGC | 1680
| CCAGCTCCGA | GCTGCAGCTG | GGCTTGGTGC | TGGCATCCCT | GGACTTGGAG | TTGGTGTCGG | 1740
| CGTCCCTGGA | CTTGGAGTTG | GTGCTGGTGT | TCCTGGACTT | GGAGTTGGTG | CTGGTGTTCC | 1800
| TGGCTTCGGG | GCAGTACCTG | GAGCCCTGGC | TGCCGCTAAA | GCAGCCAAAT | ATGGAGCAGC | 1860
| AGTGCCTGGG | GTCCTTGGAG | GGCTCGGGGC | TCTCGGTGGA | GTAGGCATCC | CAGGCGGTGT | 1920
| GGTGGGAGCC | GGACCCGCCG | CCGCCGCTGC | CGCAGCCAAA | GCTGCTGCCA | AAGCCGCCCA | 1980
| GTTTGGCCTA | GTGGGAGCCG | CTGGGCTCGG | AGGACTCGGA | GTCGGAGGGC | TTGGAGTTCC | 2040
| AGGTCTTGGG | GGCCTTGGAG | GTATACCTCC | AGCTGCAGCC | GCTAAAGCAG | CTAAATACGG | 2100
| TGCTGCTGGC | CTTGGAGGTG | TCCTAGGGGG | TGCCGGGCAG | TTCCCACTTG | GAGGAGTGGC | 2160
| AGCAAGACCT | GGCTTCGGAT | TGTCTCCCAT | TTTCCCAGGT | GGGGCCTGCC | TGGGGAAAGC | 2220
| TTGTGGCCGG | AAGAGAAAAT | GA | | | | 2242

COSMETIC COMPOSITIONS INCLUDING TROPOELASTIN ISOMORPHS

This is a continuation of Ser. No. 08/455,647 (now abandoned) filed May 31, 1995 which is a continuation Ser. No. 08/150,712 (now abandoned), filed on Nov. 10, 1993.

BACKGROUND OF THE INVENTION

The human skin consists of two layers; a superficial layer called the epidermis which is epithelial tissue and a deeper layer called the dermis that consists essentially of connective tissue. These two layers are bound together to form skin which varies in thickness from less than about 0.5 mm, to 3 or even 4 millimeters. Exposure of the skin to sun, wind, and other factors leads to skin ageing, i.e., loss of moisture in the epidermal layers of the skin, resulting in loss of elasticity, skin tone and texture as degradation of certain proteins present in the skin takes place.

The connective tissue found in skin is essentially an intricate meshwork of interacting, extracellular molecules that constitute the so-called "extracellular matrix". The extracellular matrix includes proteins that are secreted locally and are widely distributed in the extracellular matrix. The main types of proteins that make up the matrix include collagens, elastin, fibronectin and laminin. Collagens are a family of highly characteristic fibrous proteins found in all multicellular animals. They are the most abundant proteins in mammals, constituting about 25 percent of their total protein. A central feature of all collagen molecules is their stiff, triple-stranded helical structure. See, for example, Miller and Gay, "The Collagens: An Overview and Update," pp. 3-41, *Methods in Enzymology* (ed. Colowick and Kaplan), v. 144 (1987), Academic Press, Inc. Elastin, present in elastic fibers of tissues such as blood vessels and skin, gives these tissues the required ability to recoil after transient stretch. The main component of these elastic fibers is elastin, in its native state an extensively cross-linked polypeptide having a peculiar chemical composition. Approximately one third of the amino acids in elastin are glycine, 10-13 percent are proline, and over 40 percent are other amino acids with hydrophobic side chains. Elastin contains very small amounts of hydrophilic amino acids. Laminin is a large glycoprotein and a major component of basement membranes and is made by all epithelial cells that have been studied. Laminin is made up of three different subunits disulfide-bonded into an asymmetric cross-linked structure. For review see Barlow et al., "Molecular Cloning of Laminin," pp. 404-474 in *Methods in Enzymology*, v. 144 (1987) Academic Press, Inc. Fibronectin is a cell-surface and blood glycoprotein involved in a variety of cell surface phenomena. It is present in an insoluble form at the cell surface and in connective tissue, and found in soluble form in plasma. For reviews, see Ruoslahti et al., "Fibronectin: Purification, Immunochemical Properties, and Biological Activities," pp. 803-831, in *Methods in Enzymology*, supra; Hynes et al., "Isolation and Analysis of cDNA and Genomic Clones of Fibronectin and its Receptor," pp. 447-463, in *Methods in Enzymology*, v. 144, Academic Press, Inc. (1987).

Combinations of components of the extracellular matrix are often incorporated into cosmetic compositions. In some instances, normally cross-linked and insoluble elastin (i.e., insoluble in water, organic solvents, and physiological fluids such as saline, blood, and lymph) is rendered soluble using a variety of chemical and enzymatic methods. The rationale behind these procedures is that soluble elastin, and various derivatives thereof, will penetrate into the skin to a greater degree than cross-linked elastin, compensating for loss of elastin during skin ageing. The chemical and enzymatic methods designed to solubilize elastin are, however, sometimes ineffective in that they may induce unknown chemical and structural changes in the elastin molecule itself.

Moreover, the soluble precursor of insoluble elastin, called tropoelastin, is very difficult to extract and isolate and is destroyed during conventional methods for solubilizing elastin.

A further consideration when using proteins of the extracellular matrix in cosmetics concerns the degree to which the proloins produce unwanted allergic responses in the subject's skin. This is particularly problematic since the elastin used in most cosmetics primarily comes from the neck tendons of young calves, or other non-human mammals. It would be advantageous to use extracellular matrix proteins in cosmetics that avoid these problems.

SUMMARY OF THE INVENTION

The present invention pertains to a cosmetic composition including a non naturally-occurring extracellular matrix protein in combination with a cosmetic carrier. The extracellular matrix protein is preferably of human origin and has not been previously cross-linked. The protein is most preferably selected from the group consisting of soluble human procollagen and soluble human tropoelastin. The extracellular matrix protein may include at least one additional non-naturally occurring amino acid sequence moiety, the amino acid sequence moiety selected from the group consisting of a hydrophobic sequence, a hydrophilic sequence, and a lysine-rich sequence.

The amino acid sequence moiety may be preferably linked to the amino-terminus of the extracellular matrix protein by expressing a recombinantly-derived fusion protein that includes a nucleotide sequence that comprises the formula:

$$ATG-(NNN)_x-;$$

where A=adenylic acid, T=thymidylic acid, and G=guanylic acid, all joined to each other by phosphodiester bonds;

where x=1 to 20;

where N=a nucleotide base;

where $(NNN)_x$=a plurality of codons encoding: (i) a hydrophobic amino acid sequence having members selected from the group consisting of phenylalanine, tryptophan, tyrosine, and combinations of the foregoing amino acids; (ii) a hydrophilic amino acid sequence having members selected from the group consisting of aspartic acid, glutamic acid, and combinations of the foregoing amino acids; and/or (iii) a lysine-rich amino acid sequence.

In other preferred embodiments, the carboxy-terminus of the extracellular matrix protein may be preferably linked to an amino acid moiety by expressing a recombinantly-derived fusion protein that includes a nucleotide sequence that comprises the formula:

$$-(NNN)_x-TGA;$$

where A=arenylic acid, T=thymidylic acid, and G=guanylic acid, all joined to each other by phosphodiester bonds;

where x=1 to 20;

where N=a nucleotide base;

where $(NNN)_x$=a plurality of codons encoding: (i) a hydrophobic amino acid sequence having members selected from the group consisting of phenylalanine, tryptophan, tyrosine, and combinations of the foregoing amino acids; (ii) a hydrophilic amino acid sequence having members selected from the group consisting of aspartic acid, glutamic acid, and combinations of the foregoing amino acids; and/or (iii) a lysine-rich amino acid sequence.

The present invention also pertains to a cosmetic composition in which the non naturally-occurring extracellular matrix protein is an isomorphic form of the protein. The isomorph of the protein is preferably selected from the group consisting of elastin isomorphs, collagen isomorphs and fibronectin isomorphs. Most preferably, the isomorphs are of human origin and have not been previously cross-linked.

A preferred method of making a cosmetic composition is also described. The method includes providing an isomorph of a non-naturally occurring protein and combining the isomorph with a carrier. Most preferably, the protein is a soluble human tropoelastin isomorph isolated by recombinant methods, including extracting tropoelastin messenger RNA from a human cell, cloning the isomorph, and then expressing the tropoelastin isomorph. The soluble isomorph is then combined with a cosmetic carrier. A method of combatting skin ageing includes applying to skin a cosmetic comprising a non-naturally occurring extracellular matrix protein.

DETAILED DESCRIPTION OF THE INVENTION

One aspect of the invention is a cosmetic composition containing a non naturally-occurring form of an extracellular matrix protein. The term "cosmetic" or "cosmetic composition" as used herein, is intended to include all types of products which are applied in any manner directly to the person.

The term "extracellular matrix protein" refers to those macromolecules that constitute the extracellular matrix. The main classes of protein that make up the extracellular matrix are collagens, elastin, fibronectin, and laminin.

"Non naturally-occurring", when applied to the extracellular matrix proteins of the present invention means polypeptides: (i) encoded by nucleic acids using recombinant DNA methods; or (ii); synthesized by, for example, chemical synthetic methods; or (iii) separated from naturally-occurring biological materials, and purified using protein analytical procedures; or (iv) associated with chemical moieties (e.g. polypeptides; carbohydrates, fatty acids, and the like) other than those associated with the polypeptide in its naturally-occurring state; or (v) that do not occur in nature.

"Non naturally-occurring", when applied to the nucleotide sequences encoding the extracellular matrix proteins of the present invention means a portion of genomic nucleic acid, cDNA, or synthetic nucleic acid which, by virtue of its origin or manipulation: (i) is not associated with all of a nucleic acid with which it is associated in nature; or (ii) is linked to a nucleic acid or other chemical moiety other than that to which it is linked in nature; or (iii) does not occur in nature.

One significant feature of the present cosmetic compositions is that the non naturally-occurring extracellular matrix proteins of the invention have not previously been cross-linked. By "not previously cross-linked" is meant that the proteins of the cosmetic compositions:

a. are not cross-linked in the body (for example, laminin or fibronectin); or b. are a non naturally-occurring soluble precursor (for example, recombinantly derived procollagen and tropoelastin) of a cross-linked, insoluble extracellular matrix protein (e.g., collagen, elastin). The term "soluble" refers to solubility of the precursor in aqueous solutions, including water, physiological saline, blood, organic solvents, and lymph.

Procollagen is generally considered to include the soluble precursors of the various forms of collagen. The chemical structure of the various procollagens suggests that the molecule is relatively large and complex, each of the three constituent chains exhibiting an $M_r$ of between 140,000–180,000. Cloned cDNA's for human procollagen type I chains have been established. Chu et al., *Nucleic Acids Res.*, 10:5925 (1982); Myers et al., *PNAS, U.S.A.*, 78:3516 (1981), incorporated herein by reference.

Tropoelastin is a soluble polypeptide having an amino acid composition very similar to that of insoluble elastin except for the absence of cross-links and a corresponding increase in lysine residues. The total lysine content is 38 residues per mole tropoelastin compared to about 6 residues per mole in native, cross-linked elastin. Tropoelastins from all species tested share a number of features in addition to their similarity in amino acid compositions, including a molecular weight between 72 kD to 74 kD, unusually high content of hydrophobic amino acids, high solubility in concentrated solutions of short chain alcohols, and a negative temperature coefficient of solubility in salt solutions. That is, solutions of tropoelastin undergo a phase separation upon raising the temperature from 4° C. to greater than 25° C. As a result, tropoelastin is notoriously difficult to extract from epithelial cells because of its unusual solubility properties and great susceptibility to proteolytic cleavage.

Human tropoelastin, in particular, contains about 750 amino acids. The primary amino acid sequence of human tropoelastin is encoded by a 3.5 kb mRNA and consists of alternating hydrophobic domains (rich in proline, glycine, and valine) and putative cross-linking regions (rich in alanine and lysine). See Faziio, M. J. et al., *J. Invest. Dermatol.*, 91:458–464 (1988), incorporated herein by reference.

The non-naturally occurring extracellular matrix proteins of the present cosmetic compositions may be derived from mammals such as cows, sheep or pigs. Most preferably, however, the proteins are obtained from human sources. Particularly preferred proteins used in the cosmetic compositions of the invention are human tropoelastin, human procollagen and human fibronectin.

Synthetic methods for providing a variety of peptides based on collagen and tropoelastin have been described. These methods provide for synthesis of structural proteins having altered functional and chemical properties. See, U.S. Pat. No. 4,474,851 (Urry) and U.S. Pat. No. 4,898,926 (Urry), incorporated herein by reference.

Recombinant protocols for isolating non-naturally occurring extracellular matrix proteins from mammals, in particular from non-human mammals such as cows, pigs, monkeys and the like, generally involve isolating total messenger RNA from mammalian tissues or from cell lines likely to express a protein and then expressing the protein in an appropriate expression system.

Total RNA from a tissue or cell culture is isolated using conventional methods. Subsequent isolation of mRNA is typically accomplished by oligo (dT) chromatography. Messenger RNA is size-fractionated by electrophoresis and the RNA transcripts are transferred to, for example, nitrocellulose according to conventional protocols (Sambrook, J. et al., Molecular Cloning, Cold Spring Harbor Press, N.Y., 1989, incorporated herein by reference). In particular, a labelled polymerase chain reaction (PCR)-generated probe capable of hybridizing with human elastin nucleotide sequences (see Fazio et al., supra) can serve to identify RNA transcripts complementary to at least a portion of the human tropoelastin or elastin gene. For example, if Northern analysis indicates that RNA isolated from a pig epithelium hybridizes with the labelled probe, then a pig epithelium cDNA library is a likely candidate for screening and identification of a clone containing the nucleotide coding sequence for a non-naturally occurring pig homolog of tropoelastin or elastin.

Northern analysis is used to confirm the presence of mRNA fragments which hybridize to a probe corresponding to all or part of the tropoelastin or elastin protein. Northern analysis indicates the presence and size of the transcript. This allows one to determine whether a given cDNA clone is long enough to encompass the entire transcript or whether it is necessary to obtain further cDNA clones, i.e., if the length of the cDNA clone is less than the length of RNA transcripts as seen by Northern analysis. If the cDNA is not long enough, it is necessary to perform several steps such as: (i) re-screen the same library with the longest probes available to identify a longer cDNA; (ii) screen a different cDNA library with the longest probe; and (iii) prepare a primer-extended cDNA library using a specific nucleotide primer corresponding to a region close to, but not at, the most 5' available region. This nucleotide sequence is used to prime reverse transcription. The primer extended library is then screened with the probe corresponding to available sequences located at 5' to the primer. See for example, Rupp et al., Neuron, 6:811–823 (1991).

The preferred clone of the non-naturally occurring extracellular matrix protein has a complete coding sequence, i.e., one that begins with methionine, ends with a stop codon, and preferably has another in-frame stop codon 5' to the first methionine. It is also desirable to have a cDNA that is "full length", i.e. includes all of the 5' and 3' untranslated sequences. To assemble a long clone from short fragments, the full-length sequence is determined by aligning the fragments based upon overlapping sequences. Thereafter, the full-length clone is prepared by ligating the fragments together using the appropriate restriction enzymes.

As discussed above, PCR-generated probes can be used in the protocol for isolating mammalian homologues to non-naturally occurring human extracellular matrix proteins. Moreover, probes to be used in the general method for isolating vertebrate protein can include oligonucleotides, all of which encode part of a human protein nucleotide sequence. In particular, an oligodeoxynucleotide probe typically has a sequence somewhat longer than that used for the PCR primers. A longer sequence is preferable for the probe, and it is important that codon degeneracy be minimized. A representative protocol for the preparation of an oligonucleotide probe for screening a cDNA library is described in Sambrook, J. et al., Molecular Cloning, Cold Spring Harbor Press, New York, 1989. In general, the probe is labelled, e.g., $^{32}$P, and used to screen clones of a cDNA or genomic library. Alternately, an expression library can be screened using conventional immunization techniques, such as those described in Harlowe and Lane, D., Antibodies, Cold Spring Harbor Press, New York (1988). Antibodies prepared using purified protein as an immunogen are preferably first tested for cross reactivity with the homolog of protein from other species.

Recombinant methods for producing the particularly preferred, non-naturally occurring human extracellular matrix proteins of the invention are readily available. One method involves constructing a human cDNA library and screening it for extracellular matrix protein cDNAs. The resulting clones can be introduced into an expression vector system and proteins expressed and purified using standardized methods. See, for example, Sambrook et al., Molecular Cloning, Cold Spring Harbor Press, (1989). The recombinant protein can be characterized by, for example, polyacrylamide gel electrophoresis (PAGE) analysis, and N-terminal sequencing.

One specific method for isolating human tropoelastin involves screening of human cDNA library with a human or nonhuman genomic elastin probe. Positive clones are subject to sequencing and can be characterized by restriction endonuclease digestion followed by separation of DNA fragments. The smaller fragments are then used to isolate and re-screen the original cDNA library. Variations in sequence among cDNAs will indicate the presence of isomorphic forms of the protein (see below). The cDNA library is conveniently obtained from either commercial sources (e.g., Clontech, Palo Alto, Calif.) or it can be fabricated by isolating poly(A)$^+$ RNA from, for example, a fetal human aorta. The RNA isolated is used to synthesize cDNA by the RNaseH method and the cDNA inserted into, for example, a lambda phage (e.g. lambda gt 10).

Other methods rely on polymerase chain reaction (PCR) amplification of DNA, permitting the use of small samples for analysis. This technique depends upon the ability to amplify small amounts of epidermal mRNA or DNA using PCR and is based on procedures outlined in standard protocols. See, for example, Sambrook et al., supra. A sample comprising as few as a thousand to as many as hundred thousand epithelial cells is extracted to release total RNA. The RNA is converted to cDNA by using reverse transcriptase. See Example 2. The cDNA created is immediately amplified in the same reaction mixture using PCR. Primers for the PCR reaction are designed to hybridize to opposite ends of the tropoelastin messenger RNA sequence, thus amplifying the entire mRNA segment.

To obtain maximum specificity and yield in PCR, one must adjust a variety of reaction parameters, well known to those of ordinary skill in the art. The primers should have 40–60% G+C content, no long stretches of any one base, and no interprimer complementarity longer than two bases, especially at the 3' ends. Given these conditions, the following steps may increase the specificity of PCR: the reaction can be run with primer, template, and dNTP concentrations in the middle of the recommended range, using 2.5 units of Taq DNA polymerase, using an annealing temperature at least 10 degrees C. lower than optimal. If nonspecific products are observed, one may optimize the annealing temperature and adjust the primer and dNTP concentrations. Exemplary 25-mer PCR primer sequences and their position on the tropoelastin nucleotide sequence (as per Fazio et al., supra) are shown in Tables 1 and 2 for the 5' and 3' ends of tropoelastin, respectively. In Table 1 the base immediately upstream of the adenine in the start codon (ATG) is nucleotide number 1. Table 2 shows sequences complementary to the primary transcript of human tropoelastin at the 3' end. Similar primers may be generated by those of ordinary skill in the art from known mRNA sequences of other proteins. Once the appropriate clones have been isolated, the extracellular matrix proteins may be expressed and purified.

TABLE 1

HUMAN TROPOELASTIN PCR PRIMER DESIGN (5' END)

| SEQ ID NO.: | POSITION | GC % |
|---|---|---|
| 1 | −10 → −15 | 64 |
| 2 | −11 → −14 | 60 |
| 3 | −12 → −13 | 60 |
| 4 | −13 → −12 | 60 |
| 5 | −14 → −11 | 64 |
| 6 | −15 → −10 | 64 |
| 7 | −16 → −9 | 68 |
| 8 | −17 → −8 | 68 |
| 9 | −18 → −7 | 64 |
| 10 | −19 → −6 | 64 |
| 11 | −20 → −5 | 64 |
| 12 | −21 → −4 | 64 |
| 13 | −22 → −3 | 64 |
| 14 | −23 → −2 | 68 |
| 15 | −25 → −1 | 68 |
| 16 | −27 → −3 | 68 |
| 17 | −28 → −4 | 68 |
| 18 | −29 → −5 | 68 |
| 19 | −30 → −6 | 68 |
| 20 | −31 → −7 | 68 |

TABLE 2

HUMAN TROPOELASTIN PCR PRIMER DESIGN (3' END)

| SEQ ID NO.: | POSITION | GC % |
|---|---|---|
| 21 | −5 → −20 | 64 |
| 22 | −6 → −19 | 68 |
| 23 | −7 → −18 | 68 |
| 24 | −8 → −17 | 68 |
| 25 | −9 → −16 | 68 |
| 26 | −10 → −15 | 68 |
| 27 | −11 → −14 | 68 |
| 28 | −12 → −13 | 64 |
| 29 | −13 → −12 | 64 |
| 30 | −14 → −11 | 64 |
| 31 | −15 → −10 | 60 |
| 32 | −1 → −9 | 60 |
| 33 | −17 → −8 | 60 |
| 34 | −18 → −7 | 56 |
| 35 | −19 → −6 | 52 |

Expression systems utilize prokaryotic and/or eukaryotic (i.e., yeast, human) cells. See, for example, "Gene Expression Technology", Volume 185, *Methods in Enzymology*, (ed. D. V. Goeddel), Academic Press Inc., (1990) incorporated herein by reference. A large number of vectors have been constructed that contain powerful promoters that generate large amounts of mRNA complementary to cloned sequences of DNA introduced into the vector. For example, and not by way of limitation, expression of eukaryotic nucleotide sequences in *E. coli* may be accomplished using lac, trp, lambda, and recA promoters. See, for example, "Expression in *Escherichia coli*", Section II, pp. 11–195, V. 185, *Methods in Enzymology*, supra; see also Hawley, D. K., and McClure, W. R., "Compilation and Analysis of *Escherichia coli* promoter DNA sequences", Nucl. Acids Res., 11:4891–4906 (1983), incorporated herein by reference. Expression of human tropoelastin in a recombinant bacterial expression system can be readily accomplished. See Example 4.

Yeast cells suitable for expression of the proteins of the invention include the many strains of *Saccharomyces cerevisiae* as well as *Pichia pastoris*. See. "Heterologous Gene Expression in Yeast", Section IV, pp. 231–482, V. 185, *Methods in Enzymology*, supra, incorporated herein by reference. Moreover, a large number of vector-mammalian host systems known in the art may be used. See, Sambrook et al., Volume III, supra and "Expression of Heterologous Genes in Mammalian Cells", Section V, pp. 485–596, V. 185, *Methods in Enzymology*, supra, incorporated herein by reference.

Suitable expression systems include those that transiently or stably expressed DNA and those that involve viral expression vectors derived from simian virus 40 (SV 40), retroviruses, and baculoviruses. These vectors usually supply a promoter and other elements such as enhancers, splice acceptor and/or donor sequences, and polyadenylation signals. Possible vectors include, but are not limited to, cosmids, plasmids or modified viruses, but the vector system must be compatible with the host cell used. Viral vectors include, but are not limited to, vaccinia virus, or lambda derivatives. Plasmids include, but are not limited to, pBR322, pUC, or Bluescript® (Stratagene) plasmid derivatives. Recombinant molecules can be introduced into host cells via transformation, transfection, infection, electroporation, etc. Generally, introduction of protein molecules into a host is accomplished using a vector containing protein DNA under control by regulatory regions of the DNA that function in the host cell.

In particular, expression systems that provide for overproduction of a recombinant extracellular matrix protein can be prepared using, for example, the methods described in U.S. Pat. No. 4,820,642 (Edman et al., Apr. 11, 1989), incorporated herein by reference. The general requirements for preparing one form of expression vector capable of overexpression are: (1) the presence of a gene (e.g., a prokaryotic gene) into which an extracellular matrix deoxyribonucleotide sequence can be inserted; (2) the promoter of this prokaryotic gene; and (3) a second promoter located upstream from the prokaryotic gene promoter which overrides the prokaryotic gene promoter, resulting in overproduction of the extracellular matrix protein. The second promoter is obtained in any suitable manner.

Alternate methods of expressing the proteins of the invention involve generation of transgenic animals, especially mammals such as cows and goats. A "transgenic animal" is an animal having cells that contain DNA which has been artificially inserted into a cell, which DNA becomes part of the genome of the animal which develops from that cell. The preferred DNA contains nucleotide sequences that encode soluble, extracellular matrix proteins and may be entirely foreign to the transgenic animal or may be homologous to the natural gene of the transgenic animal, but which is inserted into the animal's genome at a location which differs from that of the natural gene. Once the polypeptide is expressed, it may be isolated and purified by standard methods including chromatography (e.g., ion exchange, affinity, and sizing column chromatography), centrifugation, differential solubility, or by any other standard technique for the purification of proteins. See, for example, R. K. Scopes, "Protein Purification; principles and practice", 2nd edition, Springer-Verlag, New York, 1987, incorporated herein by reference. For immunoaffirmity chromatography in particular, an extracellular matrix protein of the invention encoded by human nucleotide sequences may be isolated by binding it to an affinity column comprising antibodies that were raised against that protein, and were affixed to a stationary support. Alternatively, affinity tags such as influenza coat sequence, and glutathione-S-transferase can be attached to the proteins of the invention to allow easy purification by passage over an appropriate affinity column.

The non-naturally occurring extracellular matrix proteins of the present cosmetic compositions preferably include a moiety designed to improve or enhance the protein's function. For example, the proteins of the present invention can be linked to a moiety that: (i) enhances the skin penetration capabilities of the protein; (ii) enhances the water or oil solubility of the protein; and/or (iii) enhances the ability of the protein to act as a surfactant. These additional moieties may be present in the naturally occurring (i.e. native) protein. Nevertheless, if they are present in the native protein, the additional moieties: (i) are linked to the present, non-naturally occurring extracellular matrix proteins of the invention at a different position than they are in the native protein; and/or (ii) are present in the non-naturally occurring extracellular matrix proteins of the invention in amounts that differ from those that are in the native protein.

These additional moieties can include a variety of substances and chemical compounds, including, but not limited to liposomes, fatty acids, carbohydrates, lipids, proteins and the like. The most preferred moieties are peptide sequences. The additional sequences can be located at any position in the protein chain. Preferably, they are located at the amino-terminal end of the protein, the carboxy-terminal end of the protein, or both amino and carboxy termini.

Additional moieties may be introduced into the proteins at the nucleotide level by expressing fusion proteins in the appropriate expression system such as in Example 3. Further aspects of the invention therefore pertain to cosmetics in which the non-naturally occurring extracellular matrix proteins are encoded by non-naturally occurring nucleotide sequences that may have additional nucleotide sequences combined with them. These additional nucleotide sequences preferably encode amino acid sequence moieties selected from the group consisting of hydrophilic amino acid sequences, hydrophobic amino acid sequences, lysine-rich amino acid sequences, and combinations of the foregoing sequences.

The additional nucleotide sequences may be linked so that the extracellular matrix protein of the invention, when expressed in a suitable expression system, contains the additional amino acid moieties either: (i) internally; (ii) at the amino-terminus, the carboxy-terminus, and/or both amino and carboxy-termini of the protein.

In particular, the additional nucleotide sequences have the formula (I):

where A=adenylic acid, T=thymidylic acid, and G=guanylic acid, all joined to each other by phosphodiester bonds;

where x=1 to 20;

where N=a nucleotide base, such as for example, adenine, thymine, cytosine, guanine, uracil;

where (NNN)$_x$=a plurality of codons.

The term "N", can also include modified bases such as, but not limited to, 4-acetylcytidine, 5-(carboxyhydroxymethyl) uridine, 2'-O-methylcytidine, dihydrouridine, the methylpseudouridines, inosine, 1-methyladenosine, 1-methylguanosine, N6-methyladenosine, and others.

Nucleotide sequences of this formula may be linked to the nucleotide sequence of an extracellular matrix protein of the invention so that the amino-terminal end of the encoded protein contains a hydrophobic amino acid sequence moiety having amino acids selected from the group consisting of, for example, phenylalanine (encoded by the triplets UUU and UUC), tryptophan (encoded by the triplet UGG), proline (encoded by the triplets CCU, CCC, CCA, and CCG), glycine (encoded by the triplets GGU, GGC, GGA, and GGG), valine (encoded by the triplets GUU, GUC, GUA, and GUG) and combinations of the foregoing amino acids. Likewise, additional nucleotide sequences encoding for amino acids that are to be linked at the amino-terminus can also encode hydrophilic amino acid sequence moieties having amino acids selected from the group consisting of, for example, aspartic acid (encoded by the triplets GAU and GAC), glutamic acid (encoded by the triplets GAA and GAG), and combinations of the foregoing amino acids. Further, nucleotide sequences can include lysine-rich amino acid sequence moieties (encoded by the triplets AAA and AAG). The term "lysine-rich" means amino acid sequences containing at least 30 percent lysine residues.

Additional nucleotide sequences may also encode amino acid moieties that can be linked at the carboxy-terminus of the extracellular matrix protein. In this case, the added nucleotides have the formula (II):

where A=adenylic acid, T=thymidylic acid, and G=guanylic acid, all joined to each other by phosphodiester bonds;

where x=1 to 20;

where N=a nucleotide base, such as for example, adenine, thymine, cytosine, guanine, uracil;

where (NNN)$_x$=a plurality of codons.

The term "N", can also include modified bases such as, but not limited to, 4-acetylcytidine, 5-(carboxyhydroxymethyl)uridine, 2'-O-methylcytidine, dihydrouridine, the methylpseudouridines, inosine, 1-methyladenosine, 1-methylguanosine, N6-methyladenosine, and others.

The codons can encode a hydrophobic amino acid sequence moiety having amino acids selected from the group consisting of, for example, phenylalanine, tryptophan, proline, glycine, valine, and combinations of the foregoing amino acids. Likewise, hydrophilic and lysine-rich amino acid moieties can be added at the carboxy-terminus of the protein of the invention, using nucleotides encoding amino acid sequences as described above. Hydrophobic amino acid sequences tend to increase the lipid solubility of the protein of the invention. Hydrophilic amino acids serve to increase the water solubility of the protein. Lysine-rich amino acid sequences enhance the cross-linking of the extracellular matrix protein.

Positioning sequence moieties at both the amino and carboxy-termini of the proteins of the invention will enhance the amphipathic properties of the extracellular matrix protein. "Amphipathic" refers to a molecule that has both hydrophilic and hydrophobic groups. Amphipathic molecules are good emulsifiers (i.e., they can disperse one liquid into a second, immiscible liquid) and surfactants (i.e., they can reduce the surface tension of liquids or reduce interfacial tension between two liquids or a liquid and a solid).

Additional moieties may also be introduced into the proteins of the invention by conjugating the moieties to the expressed extracellular matrix protein using a variety of well-characterized linker molecules. Those of ordinary skill in the art will recognize that a large variety of possible linkers can be used with the proteins of the invention. See, for example, *Contributions to Microbiology and Immunology*, J. M. Cruse and R. E. Lewis, Jr (eds), Carger Press, New York, (1989), the entire contents of which are incorporated herein by reference. The conjugation of the proteins of the invention to another moiety (e.g. hydrophilic amino acid sequences) can be accomplished by any chemical reaction that will bind the two molecules so long as both molecules retain their respective activity. This linkage can include many chemical mechanisms, for instance covalent binding, affinity binding, intercalation, coordinate binding and complexation.

The preferred binding is, however, covalent binding. The covalent binding can be achieved either by direct condensation of existing side chains or by the incorporation of external bridging molecules. Many bivalent or polyvalent linking agents are useful in coupling protein molecules to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myesthenia Gravis by toxin-acetylcholine receptor conjugates." *Jour. Immun.* 133:1335-2549; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity". *Immunological Reviews* 62:185-216; and Vitetta et al., supra).

Preferred linkers for coupling a moiety to the proteins of the invention are described in the literature. See, for example, Ramakrishnan, S. et al., *Cancer Res.* 44:201-208 (1984) describing use of MBS (M-maleimidobenzoyl-N-hydroxysuccinimide ester). See also, Umemoto et al. U.S. Pat. No. 5,030,719, describing use of a halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride (see Example 4, supra); (ii) SMPT (4-succinimidyloxycarbonyl-alpha-methyl-alpha-(2-pyridyl-dithio)-toluene (Pierce Chem. Co., Cat. #21558G); (iii) SPDP (succinimidyl-6[3-(2-pyridyldithio) propionamido]hexanoate (Pierce Chem. Co., Cat #21651G); (iv) Sulfo-LC-SPDP (sulfosuccinimidyl 6[3-(2-pyridyldithio)propianamide]hexanoate (Pierce Chem. Co. Cat. #21650G); and (v) sulfo-NHS (N-hydroxysulfosuccinimide: Pierce Chem. Co., Cat. #24510) conjugated to EDC.

The linkers described above contain components that have different attributes, thus leading to molecules with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form molecules with increased stability. Disulfide linkages, are in general, less stable than other linkages because the disulfide linkage is cleaved in vivo, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodiimide coupling reaction alone.

A further aspect of the invention is a cosmetic composition that includes an isomorphic form of the extracellular matrix proteins. An interesting and provocative feature of extracellular matrix proteins is that multiple polypeptide products may be encoded from a single DNA sequence. It has been shown that elastin, fibronectin and collagen DNA sequences reveal considerable variability in their primary nucleotide sequences. See, for example, Fazio et al., Lab. Invest., 58 (3):270-277 (1988), incorporated herein by reference. Specifically, several lines of evidence suggest that the differences in the primary nucleotide sequence noted among human tropoelastin cDNA, human fibronectin cDNA and human procollagen cDNA are due to alternative splicing, a mechanism for the generation of multiple protein isoforms from single genes. Briefly, most eukaryotic DNA protein coding genes contain sequences present in the corresponding mature mRNA in discontinuous genomic DNA segments (exons) interspersed among sequences (introns) that do not form a part of the mature mRNA. These intron sequences are precisely excised by a multistep process. The majority of instances studied so far, each and every one of the exons present in a gene are incorporated into one mature mRNA through the invariant ligation of consecutive pairs of donor and acceptor splice sites, removing every intron. This type of "constitutive" splicing yields a single gene product from each transcriptional unit even when its coding sequence is split into many exons.

There are instances, however, in which nonconsecutive exons are joined in the processing of some, but not all, transcripts from a single gene. This "alternative" pattern of splicing can exclude individual exon sequences from the mature mRNA in some transcripts but include them in others. The use of such alternative splicing patterns in transcripts from a single gene yields mRNA's with different primary structures. When the exons involved contain translated sequences, these alternatively spliced mRNA's will encode related but distinct proteins, hereinafter referred to as "isomorphs". The capacity to generate different, but closely related protein isomorphs by alternative splicing increases significantly the phenotypic variability that can be obtained from single genes such as fibronectin, collagen, or elastin.

The consequences of alternate splicing of protein mRNA are significant. In fibronectin, alternative splicing has been shown to lead to synthesis of isomorphs of the protein with different physical, chemical, and functional properties. Kornblitth, R. et al., EMBO J., 4:1755 (1985).

Table 3 below summarizes the available information on isomorphic forms of human tropoelastin.

TABLE 3

ISOMORPHS OF HUMAN TROPOELASTIN

| Human elastin sequence | Deleted Exons | Reference | Exon Location* |
|---|---|---|---|
| cHDE 1 | 4 | (1) | |
| cHDE 2 | 4 | (1) | |
| cHDE 3* | 12A | (1) | 1415–1432 |
| | 13 | | 1358–1414 |
| cHDE4* | 4 | (1) | 2051–2104 |
| | 4A | | 2105–2149 |
| | 12A | | 1415–1432 |
| cHDE 5* | 12A | (1) | 1415–1432 |
| cHDE 6 | 4, 12A | (1) | |
| cHDE 7 | 4, 12A | (1) | |
| CHEL 2 | none | (2) | |
| CHEL 3* | 10 | (2) | 1640–1765 |
| CHEL 4* | 4 | (2) | 2051–2104 |
| | 10 | | 1640–1765 |
| | 13 | | 1358–1414 |
| cHE 1 | 4 | (3) | |
| cHE 2* | 4 | (3) | 2051–2104 |
| | 4A | | 2105–2149 |

TABLE 3-continued

ISOMORPHS OF HUMAN TROPOELASTIN

| Human elastin sequence | Deleted Exons | Reference | Exon Location* |
|---|---|---|---|
| cHE 3 | none | (3) | |
| cHE 4* | 4 | (3) | 2051–2104 |
| | 13 | | 1358–1414 |

*Base pair numbering of deleted exons according to Fazio et al., (reference 1)
\*Unique isomorph sequence combinations
(1)-Pazio et al., J. Invest. Derm., 91: 458 (1988)
(2)-Indik et al., Proc. Nat. Acad. Sci. USA, 84: 5680 (1987)
(3)-Fazio et al., Lab. Invest., 58: 270 (1988)

Preparation of isomorphic forms of extracellular matrix proteins is relatively straightforward, once the protein message has been isolated. For example, once the known tropoelastin messenger RNA has been amplified by the PCR method, one or more forms of the tropoelastin messenger RNA sequence are present in sufficient quantity for analysis. The presence or absence of any particular exon in the amplified sequence can be determined by cloning the amplified cDNA and determining the actual nucleotide sequence of the cloned gene. Alternately, the presence or absence of any particular exon in the amplified sequence can be determined by preparing a series of probes of DNA based on known exon sequences (see Table 3 and references cited therein). The amplified DNA can be probed by hybridization for the presence or absence of each exon without directly sequencing the DNA. This method is preferable to the method described immediately above in that it is less time consuming and expensive. The DNA hybridization probes identify any missing exons and describe the sequence of the messenger RNA accurately enough so that it can be constructed in an expression system for eventual expression of that precise tropoelastin isomorph.

It is conceivable that the different isomorphs of tropoelastin which exist (based upon differences in the coding regions of tropoelastin messenger RNA) will also have altered biological properties. We note that tropoelastin exon 13 contains lysyl residues, potentially involved in cross-linking. Thus, covalent intermolecular cross-links between tropoelastin polypeptide may be affected by the deletion or insertion of exon 13 in different isomorphs. Of the 14 total known human tropoelastin sequences (cHDE, cHEL and cHE): three are missing exon 4; two are missing no exons; and two are missing exons 4 and 12A. The remaining 7 of 14 sequences (marked with the asterisk in Table 3) are unique isomorphs.

Cosmetic compositions of the present invention containing non-naturally occurring extracellular matrix proteins include, but are not limited to, those containing the primary amino acid sequence of elastin, collagen, their soluble precursors, isomorphs thereof, and the like. The non-naturally occurring extracellular matrix proteins may include altered sequences in which functionally equivalent amino acid residues are substituted for residues within the sequence, resulting in a silent change. As alluded to previously with regard to the additional amino acid sequence moieties of the invention, a striking feature of the genetic code is its degeneracy; 61 codons (i.e., triplets) represent 20 amino acids. Almost every amino acid except tryptophan and methionine is represented by several codons. Often the base in the third position of a codon is not significant, because those amino acids having 4 different codons differ only in the third base. This feature, together with a tendency for similar amino acids to be represented by related codons, increases the probability that a single, random base change will result in no amino acid substitution or in one involving an amino acid of similar character. For example, a change of CUC to CUG has no effect since both codons represent leucine; a change of CUU to AUU results in replacement of leucine with isoleucine, a closely related amino acid. According to the invention, therefore, an amino acid is "functionally equivalent" compared with the known sequences of proteins if the amino acid sequence contains one or more amino acid residues within the sequence which can be substituted by another amino acid of a similar properties which acts in a functionally equivalent way to the original amino acid. Substitutes for an amino acid within the sequence may be selected from other members of the class to which the amino acid belongs. The non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid.

Substitutions are chosen for their effect on: (i) maintaining the structure of the peptide backbone in the area of the substitution, for example, as a sheet or helical conformation; (ii) maintaining the charge or hydrophobicity of the molecule; or (iii) maintaining the bulk of the side chain. The substitutions that in general are expected to induce greater changes are those in which: (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl, or (e) a residue having a bulky side chain, e.g., phenylalanine, is substituted for one (or by) one not having such a side chain, e.g., glycine.

Most deletions and insertions in the proteins, however, are not expected to produce radical changes in the characteristics of the protein. Nevertheless, when it is difficult to predict the exact effect of the substitution, deletion, or insertion in advance of doing so, one skilled in the art will appreciate that the effect will be evaluated using routine screening assays as described below. For example, a change in the immunological character of a given protein, such as binding to a given antibody, is measured by an immunoassay such as a competitive type immunoassay. A change in solubility may be assayed by skin penetration tests.

Also included within the scope of the invention are cosmetic preparations in which the extracellular matrix proteins are differentially modified during or after translation either by exploiting in vivo processing activity of a host or by in vitro chemical means, e.g., by phosphorylation, glycosylation, crosslinking, acylation, proteolytic cleavage, linkage to an antibody molecule, membrane molecule or other ligand, (Ferguson, et al., 1988, Ann. Rev. Biochem. 57:285–320).

In addition, the nucleic acid sequences encoding proteins of the invention may be engineered so as to modify processing or expression. For example, and not by way of limitation, nucleotide sequence(s) encoding the non-naturally occurring extracellular matrix proteins may be combined with a promoter sequence and/or a ribosome binding site using well characterized methods, and thereby facilitate harvesting or bioavailability.

Additionally, a given nucleotide sequence can be mutated in vitro or in vivo, to create variations in coding regions and/or form new restriction endonuclease sites or destroy preexisting ones, to facilitate further in vitro modification. Any technique for mutagenesis known in the art can be used including, but not limited to, in vitro site-directed mutagenesis (Hutchinson, et al., 1978, J. Biol. Chem. 253:6551), use of TAB® linkers (Pharmacia), PCR-directed mutagenesis, and the like.

Also included are protein fragments useful in the cosmetic compositions of the invention. In addition to generating fragments of protein from expression of cloned partial sequences of protein DNA, fragments of the proteins can be generated directly from the intact protein. Proteins are specifically cleaved by proteolytic enzymes, including, but not limited to, trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine. Alternate sets of cleaved polypeptide fragments are generated by preventing cleavage at a site which is susceptible to a proteolytic enzyme. For example, reaction of the $\epsilon$-amino groups of lysine with ethyltrifluorothioacetate in mildly basic solution yields a blocked amino acid residue whose adjacent peptide bond is no longer susceptible to hydrolysis by trypsin. Goldberger et al. Biochem., 1:401 (1962). Treatment of such a polypeptide with trypsin thus cleaves only at the arginyl residues.

Non-naturally occurring extracellular matrix proteins also can be modified to create peptide linkages that are susceptible to proteolytic enzyme catalyzed hydrolysis. For example, alkylation of cysteine residues with $\beta$-halo ethylamines yields peptide linkages that are hydrolyzed by trypsin. Lindley, Nature, 178:647 (1956). In addition, chemical reagents that cleave polypeptide chains at specific residues can be used. Withcop, Adv. Protein Chem. 16:221 (1961). For example, cyanogen bromide cleaves polypeptides at methionine residues. Gross & Witkip, J. Am Chem Soc., 83:1510 (1961). Thus, by treating the proteins of the invention with various combinations of modifiers, proteolytic enzymes and/or chemical reagents, numerous discrete overlapping peptides of varying sizes are generated. These peptide fragments can be isolated and purified from such digests by chromatographic methods.

Alternatively, non-naturally occurring extracellular matrix proteins can be synthesized using an appropriate solid state synthetic procedure. Steward and Young, *Solid Phase Peptide Synthesis*, Freemantle, San Francisco, Calif. (1968). A preferred method is the Merrifield process. Merrifield, *Recent Progress in Hormone Res.*, 23:451 (1967).

The non-naturally occurring extracellular matrix proteins of the invention may be capable of producing an anti-protein immune response. Use of soluble isomorphic forms of the proteins of the invention may serve to ameliorate this immune reaction, as discussed below. Alternately, or in addition, the amino acid sequence of the non-naturally occurring extracellular matrix protein may be analyzed in order to identify portions of the molecule which may be associated with decreased immunogenicity. For example, the amino acid sequence may be subjected to computer analysis to identify surface epitopes which present computer-generated plots of antigenic index, an amphophilic helix, amphiphilic sheet, hydrophilicity, and the like.

Once the extracellular matrix protein of the present invention is obtained, it can be fabricated into a cosmetic composition by combining the protein with a cosmetic carrier. The cosmetic carrier may take the form of fatty or nonfatty creams, milky suspensions or emulsion-in-oil or oil-in-water types, lotions, gels or jellies, colloidal or noncolloidal aqueous or oily solutions, pastes, aerosols, soluble tablets or sticks. The amount of preferred soluble, extracellular matrix protein contained in the cosmetic carriers according to the invention may vary between wide limits, depending upon the formulation, and the frequency of use of the composition. Generally, the carrier contains from about 0.001% to about 10% by weight of the proteins of the invention. Preferred ranges are about 0.1% to about 10%.

Extracellular matrix proteins according to the invention may also combined with surface active agents of the anionic, cationic or nonionic type, emulsifying agents, perfumes, solvents, fats, oils and mineral wax, fatty acids and derivatives thereof alcohols and derivatives thereof, glycols and derivatives thereof, glycerol and derivatives thereof, lanolin, beeswax, oleic acid, spermaceti, almond oil, castor oil, sorbitol and derivatives thereof, tracancanth gum, clay, magnesia, talc, metal stearates, chalk, magnesium carbonate, and the like. These materials are well-known in the cosmetic art and are discussed, for example, in Remington's *Pharmaceutical Science*, McCutcheon's *Detergents*, and Sagarin's *Science and Technology of Cosmetics*, all of which are incorporated herein by reference. Exemplary cosmetic compositions used according to the present invention are given in Example 1.

The cosmetic compositions used in the method according to the invention may also contain agents such as antibiotics, anti-inflammatories or anesthetics. More specifically, the soluble extracellular matrix proteins of the present invention may be combined with the following compounds, typically in a drop or ointment form with the preferred indicated typical dosages: carbenicillin (4 mg/ml); (50 mg/ml); chloramphenicol (5 mg/ml); gentamicin (8–15 mg/ml); penicillin G; polymyxin B; streptomycin; sulfacetamide; trifluridine; acyclovir; sulfadiazine; corticosteroids; nystatin; miconazole (3 mg/ml). The following anti-inflammatories may also be used in the invention; cortisone; prednisolone; dexamethasone.

The cosmetic compositions of the present invention may all contain various preservatives such as, butylated hydroxytoluene, methionine, cysteine, ascorbic acid, catalase, superoxide dismutase, glutathione, and the like. These examples are only illustrative and are not considered to limit the scope of the invention.

The ability to isolate extracellular matrix proteins from mammals, particularly humans, and provide isomorphic forms of these proteins in cosmetic compositions, lends itself to a variety of unique uses for the cosmetics of the present invention. For example, if a subject develops an immune response to a cosmetic preparation, the subject's own protein isomorph can be used in a cosmetic preparation. In this situation, the isomorph can be isolated from the subject using the methods described herein, and then combined with a suitable cosmetic carrier.

Furthermore, by using no more than routine methods, a series of cosmetic compositions can be prepared, each composition containing a different isomorphic form of a protein. In this way, cosmetics can be screened for skin responses using standard techniques. Those isomorphs that fail to generate a reaction can be used to prepare non-allergenic cosmetic compositions.

The following tests are useful in determining the efficacy of the present cosmetic compositions. One series of tests is carried out with rats in which a part of the skin of the back of the rat is depilated and then exposed to ultraviolet radiation. A cream composition, for example as described in Example 1, is applied to the exposed skin of the treated rats and to the unexposed skin of control rats. The skin of the animals treated are observed for scaling. Another series of tests may be carried out using the skin of old rats in which changes in the elastin and collagen networks and in the amount of mucopolysaccharide levels correlate well with similar changes in the skin of aged humans. See U.S. Pat. No. 4,007,266, incorporated herein by reference. In particular, male Wistar rats (about 30 months old and 400-500 g) have a skin strip of about 3 cm long by 0.5 cm wide removed from their backs parallel to the spinal cord. The strip is held stationary from the end closest to the head and a force of about 50 g applied for about 5 minutes. The length of the skin strip is measured after this traction period. This test permits a determination of the skin elasticity. Histological tests are also carried out to observe the thickness of the epidermis, the presence of ribonucleic acid in the basal cells of the epidermis, the structure of the different fibrillary elements of the dermis, such as collagen and elastin fibers, and the presence of mucopolysaccharides in the dermis. Skin specimens are preserved with Carnoy fixative or with neutral, buffered formalin solution. Skin specimens are embedded in paraffin prior to slicing by a conventional microtome. For example, presence of ribonucleic acid content is measured by toluene blue staining at a pH of 3; dermal elastin is stained by the method of Wiegert with fuschine-resorcinol and by the method of Gomori with aldehyde-fuschine.

In another embodiment, a cosmetic composition can be prepared that contains an isomorph of a human extracellular matrix protein, the isomorph being obtained from a person having certain skin characteristics. Skin of human subjects can be visually screened to select those subjects having the most youthful appearing skin. The isomorphic proteins of chosen subjects are then isolated from the subject's cells using methods described herein and are formed into a cosmetic composition for use by others with elastin that is similar immunologically or chemically. Preferred cosmetic compositions of the present invention can therefore be considered "recombinant cosmetics" and provide cosmetic preparations tailored to the individual subject.

The purity of the proteins contained with the cosmetics of the invention may be tested by purifying the proteins using conventional methods, such as SDS gel electrophoresis and arbitrarily setting a purity standard (e.g., 95% purity) that meets or exceeds that purity need to pass the conventional skin testing assays described herein. For example, the functional properties of extracellular matrix proteins of the present invention may be easily tested. For example, dermatologists have used strips of plastic adhesive tape to remove successive skin layers with each piece of tape. This removal may be verified by staining cells removed by each layer followed by histological examination. For most individuals, the outermost layer of the skin, consisting of dead cells, comprises about 12-18 layers of cells. After this number of layers has been stripped from the same site there appears what is known as a "glistening layer" of the epidermis, so-called because at this layer of tissue, fluid starts to ooze out of the living cells.

Penetration of the first layers of human skin with soluble extracellular matrix proteins of the present invention is determined by radioactively labeling the soluble proteins of the present invention, preferably with tritium. For example, elastin penetration of human skin may be determined by reacting several ml of soluble elastin with an equal volume of triatiated acetic anhydride at room temperature for several days to acylate one or more N-groups on the elastin molecule. The triatiated product is subject to repeated dialysis until a specific radioactivity (at least 500 counts per mg) is obtained. The resulting tritiated product is supplied to the forearm of a human subject. After remaining in place for several hours, tape stripings are taken from successive layers and placed in liquid scintillation counting vials for analysis. The number of counts is then determined as a function of the layers; thus the depth of penetration of the soluble protein can be determined.

A second method involves isolation of protein using recombinant methods and expression of the protein in an expression system containing radioactive amino acids, such as for example carbon-14 labeled valine. The valine, incorporated into the expressed protein, will be labeled and the expressed protein used in the tape-stripping method illustrated above. In a further method, marked areas of the back of the hand of human volunteers can be treated with the cosmetic composition of the present invention. Punch biopsies of the treated skin are taken and frozen sections are prepared. Using an antibody against the protein, (e.g., tropoelastin; see Indik Z. et al., Arch. Biochim. Biophys., 280:80-86 (1990)) immunofluorescence tests are carried out in order to visualize the location of the protein.

The present invention will now be illustrated by the following non-limiting examples in which all percentages are weight percentages.

EXAMPLE 1

Preparation of Cosmetic Compositions

CREAMS

A cream (oil-in-water) containing the active composition includes the following materials:

a) glycerol monostearate: 12.0%;
cetyl stearyl alcohol ethylene oxide adduct containing about 12 mole ethylene oxide: 1.5%;
cetyl stearyl alcohol ethylene oxide adduct containing about 20 mole ethylene oxide: 1.5%;
cetyl alcohol: 2.0%;
2-octyl-dodecanol: 10.0%;
isoctyl stearate: 8.0%;
caprylic/capric acid triglyceride: 3.0%;
methylparaben: 0.17%;
propylparaben: 0.03%; and b) distilled water: 46.8%
glycerol: 5.0% and c) extracellular matrix protein according to the present invention (prepared as explained above): 10.0%

Mixture a) is heated to approximately 70° C. and mixture b) is likewise heated to approximately 70° C. and then added while stirring to mixture a).

Stirring is continued until the cream has cooled down to approximately 30° C. Then composition c) is added while stirring and the cream is homogenized.

By the term "cream" used herein are meant all cosmetic materials which include, for instance hand creams, cleansing creams, milky lotions, cold creams, vanishing creams, hair creams, foundation creams, beauty washes, and facial packs.

EMULSIONS

Oil-in water emulsion (o/w) containing the soluble protein prepared according to the present invention includes the following materials:

a) glycerol monostearate: 3.0%;

cetyl stearyl alcohol: 2.0%;
cetyl stearyl alcohol ethylene oxide adduct containing about 12 mole ethylene oxide: 1.5%;
cetyl stearyl alcohol ethylene oxide adduct containing about 20 mole ethylene oxide: 1.5%;
glycerol monooleate: 0.5%;
2-octyl-dodecanol: 10.0%;
methylparaben: 0.17%;
propylparaben: 0.03%; and
b) distilled water: 66.3%;
glycerol: 5.0%; and
c) extracellular matrix protein according to the present invention (as in example 1): 10.0%

Mixture a) is heated to approximately 70° C. and mixture b) is likewise heated to approximately 70° C. and added while stirring to mixture a).

Stirring is continued until the o/w emulsion has cooled down to approximately 30° C. Then composition c) is added while stirring and the o/w emulsion is homogenized.

GELS

A gel containing a soluble protein according to the present invention includes the following materials:

a) distilled water: 65.1%;
polyacrylic acid (type Carbopol 940): 0.8%;
methylparaben: 0.17%;
propylparaben: 0.03%; and
b) polyoxethylene (20) sorbitan trioleate: 0.3%;
sorbitan monooleate: 0.15%;
caprylic/capric acid triglyceride: 2.5% and;
c) distilled water: 20.1%;
triethanolamine: 0.8% and;
d) extracellular matrix protein according to the present invention (as in Example 1): 10.0%

Preparation of the gel is carried out as follows:

For obtaining a), polyacrylic acid is dispersed under rapid stirring in water; then the components of b) are mixed and added under stirring to a);

likewise the aqueous triethanolamine solution c) is added under stirring;

finally, composition d) is added under stirring.

EXAMPLE 2

PCR Amplification of Elastin cDNA

Oligonucleotides Used for Amplification

Oligonucleotides are synthesized on a Biosearch DNA synthesizer. Most of the primers are mRNA-specific primers. The 5' primers and 3' primers are designed to hybridize to opposite extremes of the particular elastin mRNA sequence.

Amplification Method

RNA is reverse transcribed into cDNA using conventional methods. Briefly, a 10-μl reverse transcription reaction mixture containing 1 μg of total cellular RNA, 1×PCR buffer (20 mM Tris HCl, pH 8.3, 50 mM KCl; 2.5 mM MgCl$_2$/100 μg of bovine serum albumin per ml), 1 mM dithiothreitol, 0.5 mM dNTP, 10 units of RNasin (Promega Biotec), 0.1 μg of oligo (dT) and 100 units of BRL Moloney murine leukemia virus reverse transcriptase (Bethesda Research Laboratories) is incubated at 37° C. for 60 min, heated to 95° C. for 5–10 min, and then quick-chilled on ice. PCR is performed at a final concentration of 1×PCR buffer/50 μM dNTPs/0.1 μM each 5' and 3' primers/1×10$^6$ cpm of $^{32}$P-end-labeled primer/1 unit of Thermus aquaticus DNA polymerase (Taq polymerase)(Perkin-Elmer/Cetus) in a total volume of 50 μl. The mixture is overlaid with mineral oil and then amplified with the Perkin-Elmer Cetus thermal cycler. The amplification profile involves denaturation at 95° C. for 30 sec, primer annealing at 55° C. for 30 sec. and extension at 72° C. for 1 min.

EXAMPLE 3

Construction and Screening of a Human Skin Fibroblast cDNA Library

This method is adapted from Fazio et al., *J. Invest. Dermatol.*, 91:458–464 (1988), incorporated herein by reference.

Total RNA is isolated from cultured human skin fibroblasts (JIMM-69; established from a full-term fetus) using guanidinium isothiocyanate extraction followed by CsCl density gradient centrifugation, and used for synthesis of the cDNA library. The purified RNA is primed with oligo-dT, and first strand synthesis is catalyzed by cloned Maloney murine leukemia virus reverse transcriptase (BRL). The resultant RNA/DNA hybrid is subjected to RNase H digestion followed by second strand synthesis catalyzed by DNA polymerase I (See, Gubler, et al., *Gene* 25:263. 1983). The cDNAs are blunt-ended, using T4 polymerase, and ligated into the phage vector gZAP (Stratagene, San Diego, Calif.) using EcoRI linkers. The cDNAs are packaged using GIGA Pack Extract (Stratagene). The bacteriophage library is plated using an *E. coli* strain XL-1-Blue (Stratagene).

Initial screening of approximately 10$^6$ independent clones of the unamplified cDNA library is carried out in duplicate with two separate probes: a) cHE2, a 2.5 kb human placental elastin cDNA containing 1.5 kb of translated sequence (Fazio et al., *Lab. Invest.*, 58:270 (1988)); and b) a 5', 400 bp subclone of cHE2 isolated by EcoRI-BamHI double restriction endonuclease digestion. These probes are radio-labeled by nick transaction with a [$^{32}$P]dCTP and used to screen the library by plaque hybridization.

Clones positive to both the 2.5 kb cDNA and its 5' subclone, are subjected to plaque purification, and the isolated recombinants digested with EcoRI endonuclease. Electrophoresis on 1% agarose gel, with comparison to standard DNA markers (New England Bio Labs, Beverly, Mass.), is used to estimate the size of the inserts.

Characterization of Elastin cDNA's

The newly isolated cDNAs are characterized by restriction endonuclease digestions, followed by separation of the DNA fragments on agarose gel electrophoresis. The appropriate DNA fragments are cloned into the phage vector M13 (mp 18 and mp 19; Boehringer Mannheim, Indianapolis, Ind.), and nucleotide sequencing performed using the dideoxy chain termination method (Sanger et al., *PNAS, USA* 72:5463–5467, 1977). Sequencing primers include the universal M13 17-mer primer, as well as appropriate oligonucleotides synthesized for extension of the sequencing.

Hybridization with Exon-specific Probes

Oligonucleotide sequences specific for individual exons are selected by computer-assisted analysis of the human elastin gene structure (Indik, et al., *PNAS, USA*, 84:5680–5684, 1987; Indik et al., *Connect. Tissue Res.*, 16:197–211, 1987). The exon-specific oligonucleotides are synthesized using a modification of the phosphite method of Mateeucci and Caruthers (*J. Am. Chem. Soc.,* 103:3185–3191, 1981) employing a MilliGen (Bedford, Mass.) programmable synthesizer. The synthetic oligonucleotides are purified by reverse phase high-pressure liquid chromatograph (Varian 5000).

Exon-specific synthetic oligonucleotides are radioactively labeled at the 5'-end, with g[$^{32}$P]dATP, by a phosphate exchange reaction catalyzed by T4 polynucleotide kinase. For elucidation of the presence or absence of a specific exon sequence within the dermarl fibroblast clones, 100 ng of the insert cDNA is denatured, dotted onto nitrocellulose filters, and hybridized with 10 ng of the radiolabeled exon-specific oligonucleotide probe. Filter prehybridization is performed in a solution consisting of 0.9M NaCl, 90 mM sodium citrate (pH 7.0), 0.5% sodium dodecylsulfate, 100 ug/ml denatured salmon sperm DNA, 0.1% polyvinyl pyrrolidine, 0.1% bovine serum albumin, and 0.1% Ficoll, at 42° C. for 2 h. The hybridization, following addition of the labeled synthetic oligonucleotide probe, is carried out for 16 h in the same solution. The filters are washed at a final stringency of 0.15M NaCl, 15 mM sodium citrate, at 55° C. for 60 min.

EXAMPLE 4

Production of Recombinant Human Tropoelastin

The following procedures are adopted from those of Indik et al., *Archives of Biochemistry and Biophysics*, 280;80–86 (1990), incorporated herein by reference.

Construction of Expression Vector

Tropoelastin cDNA, reverse transcribed from the mRNA of human epidermal cells (See Example 3) is cloned into a plasmid, such as pUC8. Preferably, the 2.2 kb EcoRI/HindIII fragment of the full length tropoelastin cDNA clone, cHEL2 (Indik et al., *PNAS, USA* 84:5680, 1987), is subcloned into pUC8. The fragment includes an untranslated 5' region. Digestion of pUC8 with EcoRI and SstII removes a 48-base pair fragment containing the 5' noncoding sequence. This EcoRI/SstII fragment is then ligated to Oligomer 1 (see Indik, et al., *Arch. Biochem. Biophys.*, supra). The completed sequence includes a 5' EcoRI site, a unique NcoI site, the tropoelastin sequence, and a 3' SstII site.

The 3' region is constructed by ligating Oligomer 2 (Indik, *Arch. Biochem. Biophys.*, supra) to the HindIII site of the tropoelastin insert. Oligomer 2 contains a unique 3' HindIII site 21 base pairs upstream from the termination sequence (TGA). Oligomer 2 also contains the remainder of the tropoelastin sequence, an XbaI site, and a 3' EcoRI site. The repaired tropoelastin is cloned in the EcoRI site of pUC19, previously treated to remove HindIII, XbaI and BamHI sites. The resulting plasmid (pUC 19-tropoelastin) is cleaved at the unique NcoI site at the 5' end of the tropoelastin sequence. The cleaved tropoelastin sequence is ligated to a synthetic oligonucleotide with a start codon having formula (I): ATG-(NNN)$_x$.

Alternately, or in addition, the 3' terminus of the tropoelastin sequence can be cleaved at the HindIII site and ligated to a synthetic oligonucleotide with a stop codon having the formula (II): —(NNN)$_x$—TGA. This insert can then be cloned into an expression vector containing the signal peptide, phage promoter region, and ribosome binding domain.

The plasmid pAS-MCS72, designed to express fusion proteins, (Indik et al., *Arch. Biochem. Biophys.*, supra) is an exemplary construction. This expression plasmid is created by ligating the ECORV/PvuII fragment of pOTSNC012 (Suskilkiemar et al., *Cell;* 36:43 (1984)) which contains multiple cloning sites, into PASI EH801 (Young et al., PNAS, USA, 80:6105 (1983)) previously digested with NruI and PvuII. Thus, contained in pAS-MCS72 are a coding sequence for the influenza NS1 gene product, the P$_L$ promoter from phage lambda, the ribosome binding domain from lambda CII protein and the N antitermination function. An NcoI site within the NS1 gene provides in-frame cloning at the 5' end of the insert sequence. This construct allows for any insert protein lacking internal methionine residues (such as tropoelastin) to be separated from NS1 by CNBr cleavage.

The elastin cDNA, containing the synthetic oligonucleotides in reading frame, cloned into, for example, pAS-MCS72, is transformed into the lysogenic host *E. coli* AR120, and transforments selected using routine procedures. Bacteria bearing the expression plasmid induced by, for example, 60 mg/ml nalidixic acid, are shaken at 37° C. to allow for expression of the tropoelastin isomorph. Bacterial pellets are suspended in buffer, treated with lysozyme and then centrifuged. The pellet from the lysozyme treatment is suspended in buffer, homogenized, and centrifuged. The pellets, containing tropoelastin associated with the cell membranes, is treated with CNBr, releasing solubilized, intact tropoelastin fusion protein. Additional purification is achieved using reverse phase chromatography, or other method.

EXAMPLE 5

Preparation of Constructions for Transfections and Microinjections

Methods for purification of DNA for microinjection are well known to those of ordinary skill in the art. See, for example, Hogan et al., *Manipulating the Mouse Embryo*, Cold spring Harbor Laboratory, Cold Spring Harbor, N.Y. (1986); and Palmer et al., *Nature*, 300:611 (1982).

Construction of Transgenic Animals

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA*, 82:4438–4442 (1985)). Embryos can also be infected with viruses, especially retroviruses, modified to bear nucleic acids encoding extracellular matrix proteins.

Pluripotent stem cells derived from the inner cell mass of the embryo and stabilized in culture can be manipulated in culture to incorporate nucleic acid sequences encoding proteins of the invention. A transgenic animal can be produced from such cells through implantation into a blastocyst that is implanted into a foster mother and allowed to come to term.

Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Swiss Webster female mice are preferred for embryo retrieval and transfer. B6D2F$_1$ males can be used for mating and vasectomized Swiss Webster studs can be used to stimulate pseudopregnancy. Vasectomized mice and rats can be obtained from the supplier.

Microinjection Procedures

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia*, 47:897–905 (1991). Other procedures for introduction of DNA into tissues of animals are described in U.S. Pat. No. 4,945,050 (Sanford et al., Jul. 30, 1990).

Transgenic Mice

Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG, the mated females are sacrificed by $CO_2$ asphyxiation or cervical dislocation and embryos are recovered from excised oviducts and placed in Dulbecco's phosphate buffered saline (DPSS) with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS and in the tip of a transfer pipet (about 10–12 embryos). The piper tip is inserted into the infundibulum and the embryos transferred. After the transfer, the incision is closed by two sutures.

Transgenic Rats

The procedure for generating transgenic rats is similar to that of mice See Hammer et al., *Cell*, 63:1099–1112 (1990). Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPSS with 0.5% BSA and the embryos collected. Cumulus cells surrounding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer piper is inserted into the infundibulum. Approximately 10–12 embryos are transferred into each rat oviduct through the infundibulum. The incision is then closed with sutures, and the foster mothers are housed singly.

Embryonic Stem (ES) Cell Methods

Introduction of DNA into ES cells:

Methods for the culturing of ES cells and the subsequent production of transgenic animals by the introduction of DNA into ES cells using methods such as electroporation, calcium phosphate/DNA precipitation; and direct injection are well known to those of ordinary skill in the art. See, for example, *Teratocarcinomas and Embryonic Stem Cells, A Practical Approach*, E. J. Robertson, ed., IRL Press (1987). Selection of the desired clone containing ES cells is accomplished through one of several means. Although embryonic stem cells are currently available for mice, it is expected that similar methods and procedures as described and cited here will be effective for embryonic stem cells from different species as they become available.

In cases involving random gene integration, a clone containing nucleic acid sequences encoding the soluble extracellular matrix proteins of the invention is co-transfected with a gene encoding neomycin resistance. Alternatively, the gene encoding neomycin resistance is physically linked to the sequence encoding the soluble extracellular matrix proteins. Transfection is carried out by any one of several methods well known to those of ordinary skill in the art (E. J. Robertson, supra). Calcium phosphate/ DNA precipitation, direct injection, and electroporation are the preferred methods. Following DNA introduction, cells are fed with selection medium containing 10% fetal bovine serum in DMEM supplemented with G418 (between 200 and 500 µg/ml biological weight). Colonies of cells resistant to G418 are isolated using cloning tings and expanded. DNA is extracted from drug resistant clones and Southern blotting experiments using a transgene-specific DNA probe are used to identify those clones carrying the sequence(s). In some experiments, PCR methods are used to identify the clones of interest.

DNA molecules introduced into ES cells can also be integrated into the chromosome through the process of homologous recombination. Copecchi, *Science*, 244:1288–1292 (1989). Direct injection results in a high efficiency of integration. Desired clones are identified through PCR of DNA prepared from pools of injected ES cells. Positive cells within the pools are identified by PCR subsequent to cell cloning. DNA introduction by electroporation is less efficient and requires a selection step. Methods for positive selection of the recombination event (i.e., neo resistance) and dual positive-negative selection (i.e., neo resistance and gancyclovir resistance) and the subsequent identification of the desired clones by PCR have been described by Copecchi, supra and Joyner et al., *Nature*, 338:153–156 (1989), the disclosures of which are incorporated herein.

Embryo Recovery and ES Cell Injection

Naturally cycling or superovulated female mice mated with males are used to harvest embryos for the implantation of ES cells. It is desirable to use the C57BL165 strain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10–20 ES cells are injected into blastocysts using a glass microneedle with an internal diameter of approximately 20 µm.

Transfer of Embryos to Receptive Females

Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 gauge needle through which the blastocysts are transferred. After the transfer, the ovary and uterus are pushed back into the body and the incision is closed by two sutures. This procedure is repeated on the opposite side if additional transfers are to be made.

Identification of Transgenic Mice and Rats

Tail samples (1–2 cm) are removed from three week old animals. DNA is prepared and analyzed by Southern blot or PCR to detect transgenic founder ($F_0$) animals and their progeny ($F_1$ and $F_2$). In this way, animals that have become transgenic for the sequences encoding soluble extracellular matrix protein are identified. Because not every transgenic animal expresses the soluble extracellular matrix protein, and not all of those that do will have the expression pattern anticipated by the experimenter, it is necessary to characterize each line of transgenic animals with regard to expression of the protein in different tissues.

Production of Non-Rodent Transgenic Animals

Procedures for the production of non-rodent mammals and other animals have been discussed by others. See Houdebine and Chourrout, supra; Pursel et al., *Science* 244:1281–1288 (1989); and Simms et al., *Bio/Technology*, 6:179–183 (1988).

EQUIVALENTS

It should be understood that the preceding is merely a detailed description of certain preferred embodiments. It therefore should be apparent to those skilled in the art that various modifications and equivalents can be made without departing from the spirit or scope of the invention.

---

What is claimed:

1. A method of formulating a cosmetic composition, the method comprising steps of:

selecting a human individual on the basis of that individual having youthful-appearing skin, as compared with skin of the individual onto whom the cosmetic is to be applied;

obtaining at least two nucleic acids, each of which encodes a different tropoelastin isomorph that is present in epidermis of the selected human individual with the youthful-appearing skin;

introducing each of the identified nucleic acids into its own expression vector so that a population of expression constructs, each of which encodes a different tropoelastin isomorph, is produced, the population including vectors encoding at least two different tropoelastin isomorphs;

introducing each expression construct into a host cell so that a population of host cells, each of which has received an individual expression construct and expresses a single tropoelastin isomorph therefrom, is produced;

identifying those host cells in the population of the host cells that express one of the at least two tropoelastin isomorphs;

purifying each of the at least two tropoelastin isomorphs from the host cell that produces it; and combining the at least two purified tropoelastin isomorphs with one another in ratios at which they are found in the epidermis of the selected individual, and also with a cosmetic carrier, to form a cosmetic composition.

2. The method of claim 1 wherein the step of selecting comprises selecting a human individual other than the one onto whom the cosmetic composition is to be applied.

3. The method of claim 1 where the step of selecting comprises selecting a human individual onto whom the cosmetic composition is to be applied.

4. The method of claim 1, wherein each of the at least tow tropoelastin isomorphs is selected from the group consisting of full-length tropoelastin, a tropoelastin isomorph lacking exon 4 (residues 2100–2153 of SEQ ID NO:37), a tropoelastin isomorph lacking exon 4A (residues 2154–2198 of SEQ ID NO:37), a tropoelastin isomorph lacking exon 12A (residues 1464–1488 of SEQ ID NO:37), a tropoelastin isomorph lacking exon 13 (residues 1689–1814 of SEQ ID NO.37), a tropoelastin isomorph lacking exons 4 and 12A, a tropoelastin isomorph lacking exons 4 and 4A, a tropoelastin isomorph lacking exons 4A and 12A, a tropoelastin isomorph lacking exons 12A and 13, a tropoelastin isomorph lacking exons 4 and 13, and a tropoelastin isomorph lacking exons 4, 10, and 13.

5. The method of claim 1, wherein the step of combining comprises adding an agent selected from the group consisting of antibiotics, anti-inflammatories, anesthetics, and combinations thereof of antibiotics and anti-inflammatories, combinations of anti-inflammatories and anesthetics, combinations of antibiotics and anesthetics, and combinations of antibiotics, anti-inflammatories, and anesthetics to the compositions.

6. The method of claim 1, wherein the step of combining comprises adding an extracellular matrix selected from the group consisting of collagen, fibronectin, and laminin.

* * * * *